United States Patent
Koehler et al.

(10) Patent No.: US 10,485,492 B2
(45) Date of Patent: Nov. 26, 2019

(54) SOURCE-DETECTOR ARRANGEMENT

(71) Applicant: KONINKLIJKE PHILIPS N.V., Eindhoven (NL)

(72) Inventors: Thomas Koehler, Norderstedt (DE); Ewald Roessl, Ellerau (DE); Rolf Karl Otto Behling, Norderstedt (DE); Peter Benjamin THeodor Noel, Munich (DE); Franz Pfeiffer, Unterföhring (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 260 days.

(21) Appl. No.: 15/524,112

(22) PCT Filed: Nov. 10, 2015

(86) PCT No.: PCT/EP2015/076213
§ 371 (c)(1),
(2) Date: May 3, 2017

(87) PCT Pub. No.: WO2016/075140
PCT Pub. Date: May 19, 2016

(65) Prior Publication Data
US 2017/0319149 A1     Nov. 9, 2017

(30) Foreign Application Priority Data
Nov. 11, 2014 (EP) ..................................... 14192623

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/4035* (2013.01); *A61B 6/4085* (2013.01); *A61B 6/484* (2013.01);
(Continued)

(58) Field of Classification Search
CPC ..... A61B 6/032; A61B 6/4035; A61B 6/4085; A61B 6/484; G21K 2207/005
See application file for complete search history.

(56) References Cited

U.S. PATENT DOCUMENTS

| 7,945,018 B2 | 5/2011 | Heismann |
| 8,009,796 B2 | 8/2011 | Popescu |

(Continued)

FOREIGN PATENT DOCUMENTS

| WO | 2007074029 A1 | 7/2007 |
| WO | 2010067260 A1 | 6/2010 |

(Continued)

OTHER PUBLICATIONS

Tuohimaa et al., "Phase-contrast x-ray imaging with a liquid-metal-jet-anode microfocus source," Applied Physics Letters 91, 074104. (Year: 2007).*

(Continued)

*Primary Examiner* — Chih-Cheng Kao
(74) *Attorney, Agent, or Firm* — Larry Liberchuk

(57) ABSTRACT

The invention relates to a source-detector arrangement (11) of an X-ray apparatus (10) for grating based phase contrast computed tomography. The source-detector arrangement comprises an X-ray source (12) adapted for rotational movement around a rotation axis (R) relative to an object (140) and adapted for emittance of an X-ray beam of coherent or quasi-coherent radiation in a line pattern (21); and an X-ray detection system (16) including a first grating element (24) and a second grating element (26) and a detector element (Continued)

(6); wherein the line pattern of the radiation and a grating direction of the grating elements are arranged orthogonal to the rotation axis; and wherein the first grating element has a first grating pitch varied dependent on a cone angle ($\beta$) of the X-ray beam and/or the second grating element has a second grating pitch varied dependent on the cone angle of the X-ray beam.

14 Claims, 13 Drawing Sheets

(51) Int. Cl.
*H01J 35/14* (2006.01)
*G02B 5/18* (2006.01)

(52) U.S. Cl.
CPC ............ *G02B 5/1866* (2013.01); *H01J 35/14* (2013.01); *G21K 2207/005* (2013.01); *H01J 2235/082* (2013.01); *H01J 2235/086* (2013.01)

(56) References Cited

U.S. PATENT DOCUMENTS

| 9,453,803 | B2 | 9/2016 | Radicke | |
|---|---|---|---|---|
| 2007/0183582 | A1* | 8/2007 | Baumann | A61B 6/484 378/145 |
| 2009/0110144 | A1* | 4/2009 | Takahashi | A61B 6/484 378/62 |
| 2010/0080341 | A1* | 4/2010 | Popescu | A61B 6/032 378/19 |
| 2010/0177864 | A1* | 7/2010 | Donath | A61B 6/032 378/16 |
| 2010/0322380 | A1* | 12/2010 | Baeumer | G21K 1/06 378/62 |
| 2011/0235784 | A1* | 9/2011 | Behling | H01J 35/10 378/125 |
| 2012/0163541 | A1 | 6/2012 | Kaneko | |
| 2014/0185746 | A1 | 7/2014 | Baturin | |
| 2015/0030126 | A1* | 1/2015 | Radicke | G01N 23/04 378/62 |

FOREIGN PATENT DOCUMENTS

| WO | 2010150136 A1 | 12/2010 |
|---|---|---|
| WO | 2011070519 A1 | 6/2011 |
| WO | 2012005128 A1 | 1/2012 |
| WO | 2014125389 A1 | 8/2014 |
| WO | 2014154188 A1 | 10/2014 |

OTHER PUBLICATIONS

Weitkamp, T. et al "X-Ray Phase Imaging with a Grating Interferometer", Optics Express 6296, Aug. 8, 2005, vol. 13, No. 16.
Bech, M. et al "Quantitative X-Ray Dark-Field Computed Tomography", Phys. Med. Biology, vol. 55, 2010, pp. 5529-5539.
Yaroshenko, A. et al "Non-Binary Phase Gratings for X-Ray Imaging with a Compact Talbot Inteferometer", Opticas Express, vol. 22, No. 1, Jan. 2014, pp. 547-556.
Feldkamp, L.A. et al "Practical Cone-Beam Algorithm", J. Opt. Soc. Am. vol. 1, No. 6, Jun. 1984, pp. 612-619.
Koehler, T. et al "Iterative Reconstruction for Differential Phase Contrast Imaging using Spherically Symmetric Basis Functions", Med. Phys. vol. 38. No. 8, Aug. 2011, pp. 4542-4545.
Van Stevendaal, U. et al "Reconstruction Method for Object-Position Dependent Visibility Loss in Dark-Field Imaging", Proc. SPIE 8668, Medical Imaging 2013: Physics of Medical Imaging.

* cited by examiner

SOURCE-DETECTOR ARRANGEMENT

CROSS-REFERENCE TO PRIOR APPLICATIONS

This application is the U.S. National Phase application under 35 U.S.C. § 371 of International Application No. PCT/EP2015/076213, filed on Nov. 10, 2015, which claims the benefit of European Patent Application No. 14192623.8, filed on Nov. 11, 2014. These applications are hereby incorporated by reference herein.

FIELD OF THE INVENTION

The invention relates to differential phase-contrast imaging, including dark-field imaging. In particular, the present invention relates to a source-detector arrangement of an X-ray apparatus for grating based phase contrast computed tomography, and an X-ray apparatus for grating based phase contrast computed tomography comprising a source-detector arrangement. Further, the invention relates to a method for generating and detecting an X-ray beam with a source-detector arrangement of an X-ray apparatus for grating based phase contrast computed tomography and a method for generating an image of an object with an X-ray apparatus for grating based phase contrast computed tomography as well as a computer program product for controlling the X-ray apparatus for generating an image of an object.

BACKGROUND OF THE INVENTION

When acquiring an X-ray image, an object to be examined, e.g. a patient, is arranged between an X-ray source or generating device, e.g. an X-ray tube, and an X-ray detection system. Radiation emanating from the X-ray source is penetrating the object to be examined, subsequently arriving at the X-ray detection system. Conventional computed tomography (CT) measures the linear attenuation coefficient of objects.

In phase-contrast imaging, or phase contrast computed tomography, at least partly spatially coherent or quasi coherent radiation in a line pattern is employed. Coherent or quasi coherent X-rays penetrating the object may allow for subsequent retrieval of phase information. X-ray phase-contrast imaging is described, for example, in Weitkamp T., Diaz A., David C. et al.: "X-ray phase imaging with a grating interferometer"; Optics Express 6296, 8, Aug. 2005, Vol. 13, No. 16. Grating based phase contrast imaging systems further provide dark field images which are indicative for the small angle scattering power of the sample. This aspect is detailed in M. Bech, O. Bunk, T. Donath et al.: "Quantitative x-ray dark-field computed tomography"; Phys. Med. Biol. 55 (2010) 5529-5539.

An increase in the fan angle of an X-ray beam may lead to a reduced structure visibility. In particular in medical application, which requires large fan angles of X-ray beam due to object size, this can result in a significant loss of structure visibility.

SUMMARY OF THE INVENTION

It is an object of the present invention to provide a source-detector arrangement of an X-ray apparatus for grating based phase contrast computed tomography which overcomes at least one of the above mentioned drawbacks. It is a further object of the invention to provide a source-detector arrangement of an X-ray apparatus for grating based phase contrast computed tomography which reduces the influence of the fan angle. It is a further object of the present invention to provide an X-ray apparatus for grating based phase contrast computed tomography, which comprises the source-detector arrangement. Moreover, it is an object of the present invention to provide a method for generating and detecting an X-ray beam with a source-detector arrangement of an X-ray apparatus for grating based phase contrast computed tomography and a method for generating an image of an object with an X-ray apparatus for grating based phase contrast computed tomography and to provide a computer program for controlling the X-ray apparatus for generating an image of an object.

In a first aspect of the present invention a source-detector arrangement of an X-ray apparatus for grating based phase contrast computed tomography is presented, comprising:

an X-ray source adapted for rotational movement around a rotation axis relative to an object and adapted for emittance of an X-ray beam of coherent or quasi-coherent radiation in a line pattern;

an X-ray detection system including a first grating element and a second grating element and a detector element; wherein the line pattern of the radiation and a grating direction of the grating elements are arranged orthogonal to the rotation axis; and wherein the first grating element has a first grating pitch varied dependent on a cone angle of the X-ray beam and/or the second grating element has a second grating pitch varied dependent on the cone angle of the X-ray beam.

Herein, phase-contrast imaging is understood to include dark-field scatter imaging based on a dark-field signal resulting from ultra-small-angle scattering by sub-pixel microstructures of the sample. In phase-contrast imaging, or phase contrast computed tomography, at least partly spatially coherent or quasi coherent radiation in a line pattern is employed. Such coherent or quasi coherent X-rays penetrating the object may allow for subsequent retrieval of phase information. The term radiation can be understood herein as X-rays or an X-ray beam.

To retrieve this information, phase-shift is converted to an intensity modulation, e.g., by interferometry. For generating an according interference pattern, a first grating element or first grating, so-called phase grating, is employed, arranged between the object to be examined and an X-ray detector element. This phase grating creates an interference pattern further downstream of the beam. A second grating element or second grating, so-called analyzer grating, is arranged between the first grating element and the X-ray detector element, where the pitch of the second grating matches the period of the interference pattern generated by the first grating element. This design allows for a very sensitive ability to detect tiny deflections of the X-ray beam because this translates into small displacements of the interference pattern.

To obtain appropriate image information, a so-called phase stepping may be performed. In phase stepping, one of the phase grating element, the analyzer grating element, and the line pattern of the X-ray source is displaced laterally with respect to the others.

The present invention is based, inter alia, on the finding that by turning the grating elements and the source line pattern by 90° with respect to known arrangements, the drawbacks related to large fan angles, which are required in medical application due to object size, namely tilted or curved detectors and/or significant loss of structure visibility, can be avoided or reduced. In known arrangements for grating based differential phase contrast CT, the grating elements are typically aligned with the rotation axis. The stepping direction (i.e. the direction where the gradient of the wavefront is measured) lies in the plane of rotation. With such a known arrangement the absolute value of the real part of the complex refractive index can be reconstructed by simple filtered back-projection, where the filter is a Hilbert-filter. However, a shortcoming of this known arrangement is that the system is restricted to relatively small fan-angles. Simulation studies showed that with a flat detection system, the visibility of structures drops quickly already for fan-angle as small as 10°. This implies that for a medical application, where larger fan-angles are mandatory due to the object size, a curved detection system has to be used, which is much more difficult to manufacture.

By turning the grating elements and the source line pattern by 90° with respect to known arrangements, the projected lines of the X-ray beam are parallel across the fan angle, and thus curved or tilted detectors are no longer necessary.

Herein, the term orthogonally is understood to comprise also substantially orthogonal arrangements, in particular to comprise deviations from an exact orthogonal arrangement within ±5°.

The fan angle of the X-ray beam is understood as the angle of the X-ray beam in the plane of rotation, whereas the cone angle of the X-ray beam is understood as the angle of the X-ray beam orthogonal to the fan angle. By definition the cone angle is negative in the direction of where the take-off angle of the x-ray beam from the anode is smaller than the take-off angle at 0° cone angle. The fan angle is typically many times larger than the cone angle.

The anode angle is understood as the angle of an anode target surface with respect to a central ray (central axis) in the X-ray beam.

It is to be noted that a rotational movement around a rotation axis relative to an object may for example be realized by rotating the source-detector arrangement relative to a stationary object, or by rotating an object relative to a stationary source-detector arrangement, or a combination of both. To simplify the description herein, it will in the following usually be assumed without loss of generality that the source-detector arrangement rotates relative to the environment while a center region with the object is stationary. In the context of this description, the term coherent or quasi-coherent radiation is understood as radiation which leads to the formation of an interference pattern under given geometries and given distances of the first and second grating element.

The invention is further based on the finding, that the effect resulting from turning the line pattern and grating elements by 90° that the pitch of the grating elements as seen from the detector element depends on the cone angle of the X-ray beam can be compensated by a cone angle dependent variation of the grating pitches of the first and/or second grating elements.

This may be seen as employing a phase grating element (first grating element) and/or an analyzer grating element (second grating element) having a non-uniform or varying pitch structure with regard to the cone angle of the X-ray beam. The grating pitch of the first grating element and/or the grating pitch of the second grating element vary along a cone angle of the X-ray beam, i.e. in a direction orthogonal to the grating direction, in particular orthogonal to the longitudinal direction of the grating lines.

The grating structure of each grating element, or referred to as grating in short, may be seen as comprising individual barrier elements, each forming a barrier region, spaced apart from one another, thus forming a trench region between the barrier elements. Preferably, the trench region and the barrier region both comprise the same width, thus the trench region and the barrier region or barrier element are substantially of the same dimension.

The distance between two barrier elements or grating lines arranged adjacent to each other may be referred to as the pitch of the grating element. Thus, the pitch of a grating element is either the width of a trench region plus the width of a barrier region or, since barrier region and trench region preferably comprise the same width, the pitch of the grating element equals also two times either the width of a trench region or a barrier region. A pitch of the grating element may also be referred to as the periodicity of the grating element.

The varying pitch of the first and second grating elements along the cone angle preferably matches the effective pitch of line pattern of the radiation emitted by the anode.

For binary grating elements, for a given distance d between the first and second grating elements, the best visibility of the interference pattern can be obtained, if the quantity $$a = \frac{8d\lambda}{p_1^2}$$

is an odd integer. This integer is called the Talbot order of the interferometer. For a given Talbot order, a given distance d and a given pitch $p_1$ of the first grating element, the resulting x-ray wave-length $\lambda$ is called the design energy (since the wavelength corresponds to an energy). Note that the height of the first grating elements (or the depths of the trenches) should preferably correspond to the design energy as well since a $\pi$ or $\pi/2$ phase shift is desired (and the phase shift decreases quadratically with energy in the hard x-ray regime in the absence of k-edges). Also for non-binary gratings, there is a general relation between the distance between the first and second grating elements, the pitch of the grating elements and the x-ray wave-length, based on which visibility may be optimized. This relation may be used to compensate the modulation of the pitch of the grating elements along the cone angle. For non-binary gratings, this relation is explained in detail, for example, in A. Yaroshenko et al.: "Non-binary phase gratings for x-ray imaging with a compact Talbot interferometer", Optics Express. Vol. 22(1), January 2014, pp. 547-556, which is herewith incorporated by reference.

This arrangement has the advantage, inter alia, that shallow anode angles yielding high X-ray flux can be employed while using a large fan angle.

In an embodiment, the X-ray source comprises a source grating element with a grating direction arranged orthogonal to the rotation axis. By using a source grating element, coherent or quasi-coherent X-ray beam in a line pattern in the desired direction or orientation can be created without having to change the source of the X-ray beam, in general an anode. In the X-ray source, preferably only the source grating element has to be adapted to form the coherent or quasi-coherent X-ray beam in a line pattern in the desired direction or orientation orthogonal to the rotation axis. In addition, it has been found that a dependency on the cone angle of the pitch of the first and/or second grating element of the X-ray detection system as described below is sufficiently small when a source grating element is used such that a variation of the pitch of the first and/or second grating element is not yet necessary, in particular for cone angles smaller than ±5°, in particular for cone angles between ±1.5° and ±3.5°, in particular for cone angles of about ±2.5°.

In a further embodiment, the X-ray source includes an anode to emit the coherent or quasi-coherent radiation in a line pattern, the anode comprising strips of different radiation emission, which are arranged parallel to grating lines of the first and/or second grating element. Such an anode may also be referred to as a structured anode. Preferably, the anode is a rotary anode with a shallow anode angle, preferably an anode angle of less than 15°. The X-ray source may be further detailed as described in WO 2007/074029 A1 and/or U.S. Pat. No. 7,945,018 B2, which are both herewith incorporated by reference.

By using an anode which is adapted to emit the coherent or quasi-coherent X-ray beam in a line pattern in the desired direction or orientation, no additional source grating element is needed.

In an embodiment, the first grating pitch and/or the second grating pitch are varied uniformly along the cone angle of the X-ray beam. A uniform variation of the grating pitch may be understood as a variation that is independent of the fan-angle.

In a further embodiment, the first grating pitch and/or the second grating pitch are varied gradually along the cone angle of the X-ray beam. A gradual variation of the grating pitch may be understood as a stepwise variation, which may be realized by two or more different grating pitch sections with the same grating pitch within one section but with different grating pitches in different grating pitch sections.

In another embodiment, the first grating pitch and/or the second grating pitch are varied from a smaller grating pitch to a larger grating pitch along the cone angle of the X-ray beam.

In a further embodiment, the first grating element and/or the second grating element and/or the detector element are arranged in planes extending parallel to each other.

The turning of the grating elements and the source line pattern by 90° with respect to known arrangements has further the advantage to provide the possibility to use planar instead of curved or tilted grating elements and/or curved or tilted detector elements. Preferably, the first grating element and the second grating element and the detector element are arranged parallel to each other.

In another embodiment, the first grating element and/or the second grating element are adapted to be moveable relative to one another for providing phase stepping. In particular, the first and/or second grating element is adapted to be moveable relative to one another in a direction parallel to the rotation axis, i.e. orthogonal to the grating direction. It may be provided, for example, an apparatus for displacing the second grating element relative to the first grating element in a direction orthogonal to the radiation and orthogonal to the direction of the grating lines.

In case the X-ray source comprises a source grating element, it is preferred that the source grating element is adapted to be moveable relative to the first and second grating elements for providing phase stepping. Further, in case the X-ray source comprises a line source without a source grating, in particular a structured anode and/or a structured electron beam, it is preferred to step the line pattern of the X-ray source, i.e. it is preferred that the line pattern of the X-ray source is adapted to be moveable relative to the first and/or second grating elements for providing phase stepping.

According to another embodiment, the X-ray source comprises a rotary anode and a position sensor for detecting a recurrent deviation of an actual position from a desired position of an electron beam's focal spot on a target area of the rotary anode, and a beam deflection unit with an integrated controller for deflecting said beam based on measurement results obtained from the position sensor. This embodiment has the advantage to overcome the so-called wobble effect resulting from the fact that a rotating anode is not mounted straight on the anode shaft due to mechanical tolerances and inaccuracies during the production process. The wobble effect leads to a periodic position change of the focal spot on the anode target. The X-ray source may be further detailed as described in WO 2010/067260 A1, which is herewith incorporated by reference. Preferably, the rotary anode is a structured anode as described above.

In a further embodiment, the X-ray source comprises a structured electron beam directed to an anode to emit the coherent or quasi-coherent radiation in a line pattern. The X-ray source comprising a structured electron beam may be further detailed as described in WO 2010/067260 A1, which is herewith incorporated by reference. In a preferred embodiment, the structured electron beam is adapted to be moveable, in particular relative to the first and/or second grating element, for providing phase stepping. In particular, it is preferred that the structured electron beam is electromagnetically moveable, e.g. by an electromagnetic beam movement unit.

According to another embodiment, the X-ray source comprises a plurality of liquid metal jets providing a plurality of focal lines. Preferably, the X-ray source further comprises an electron beam structure that provides a sub electron beam to each liquid metal jet, wherein the liquid metal jets are each hit by the sub electron beam along an electron impinging portion or focal line. The X-ray source may be further detailed as described in WO 2014/125389 A1, which is herewith incorporated by reference.

In a further aspect of the present invention an X-ray apparatus for grating based phase contrast computed tomography is presented, wherein the X-ray apparatus comprises a source-detector arrangement as defined in claim 1.

In a further aspect of the present invention, a method for generating and detecting an X-ray beam with a source-detector arrangement of an X-ray apparatus for grating based phase contrast computed tomography is presented, the method comprising:

rotating an X-ray source emitting coherent or quasi-coherent radiation relative to an object around a rotation axis;

detecting the radiation by an X-ray detection system including a first grating element and a second grating element and a detector element; wherein the line pattern of the radiation and a grating direction of the grating elements are arranged orthogonal to the rotation axis; and wherein the first grating element has a first grating pitch varied dependent on a cone angle of the X-ray beam and/or the second grating element has a second grating pitch varied dependent on the cone angle of the X-ray beam.

In a further aspect of the present invention, a method for generating an image of an object with an X-ray apparatus for grating based phase contrast computed tomography is presented, the method for generating an image comprising the method for generating and detecting an X-ray beam according to claim 12, and wherein a direction of phase stepping is parallel to the rotation axis.

Preferably, existing filtered back-projection algorithms are used to reconstruct the projection of the gradient of the object's real part of refractive index in direction of the rotation axis from the measurement of the gradient of the phase front in direction of the rotation axis by the detection system. A filtered back-projection algorithm is described in L. A. Feldkamp et al.: "Practical cone-beam algorithm", J. Opt. Soc. Am. A/Vol. 1, No. 6/June 1984, p. 612-619, which is herewith incorporated by reference. The use of filtered back-projection algorithms is indicated in particular, when it is sufficient to reconstruct the first derivative of the electron density in the direction of the rotation axis.

In another embodiment, an iterative reconstruction algorithm may be used. An iterative reconstruction algorithm is described in T. Koehler et al.: "Iterative reconstruction for differential phase contrast imaging using spherically symmetric basis functions", Med. Phys. 38 (8), August 2011, p. 4542-4545, which is herewith incorporated by reference.

As mentioned earlier, the dark field signal which is indicative for the small angle scattering power of the sample can also be detected by the grating based setup. As long as the scattering is isotropic, the change of the grating direction does not lead to a change of the reconstruction algorithm, i.e. methods like the one described in U. van Stevendaal et al.: "Reconstruction method for object-position dependent visibility loss in dark-field imaging", Proc. SPIE 8668, Medical Imaging 2013: Physics of Medical Imaging, 86680Z (2013); doi: 10.1117/12.2006711 can still be used.

In a further aspect of the present invention a computer program for generating an image of an object is presented, wherein the computer program comprises program code means for causing an X-ray apparatus according to claim 11 to carry out the steps of the method for generating an image as defined in claim 13, when the computer program is run on a computer controlling the X-ray apparatus.

It shall be understood that the source-detector arrangement of an X-ray apparatus for grating based phase contrast computed tomography of claim 1, the X-ray apparatus for grating based phase contrast computed tomography of claim 11, the method for generating and detecting an X-ray beam with a source-detector arrangement of an X-ray apparatus for grating based phase contrast computed tomography of claim 12, the method for generating an image of an object with an X-ray apparatus for grating based phase contrast computed tomography of claim 13, and the computer program for controlling an X-ray apparatus for generating an image of an object of claim 14, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
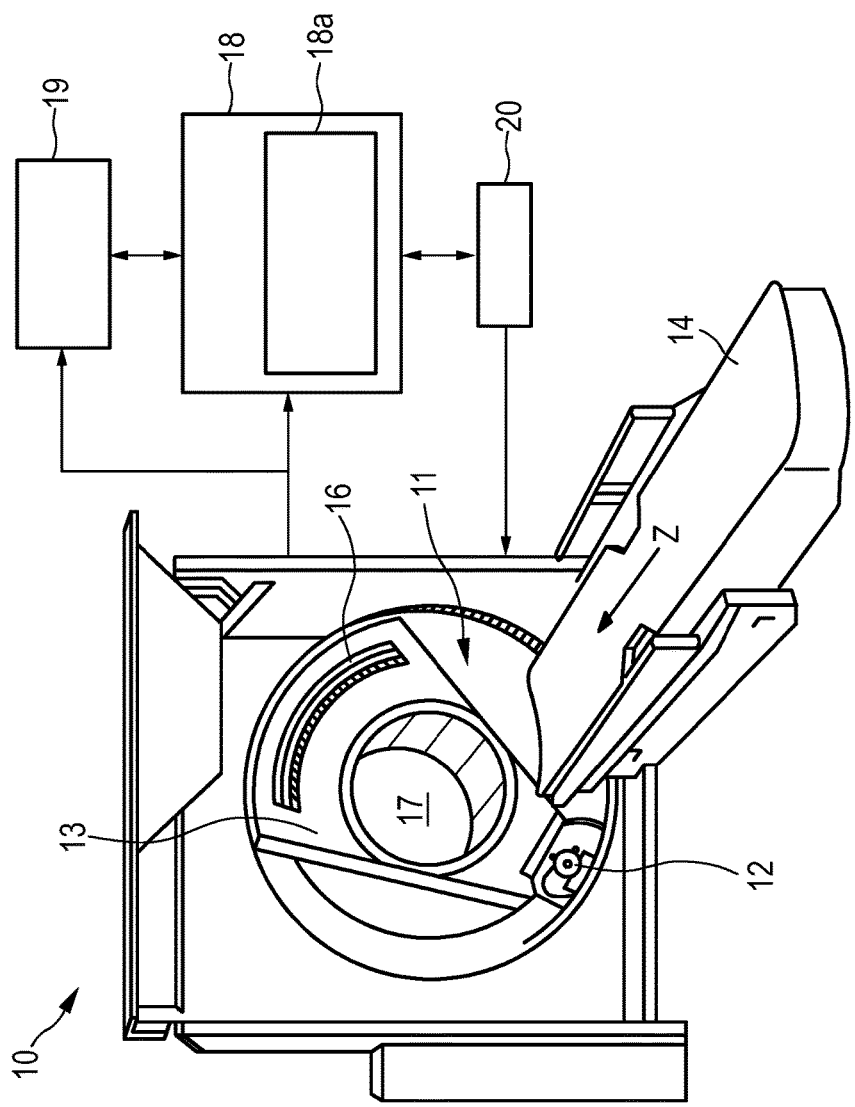
FIG. 1 shows schematically and exemplarily an embodiment of an X-ray apparatus for grating based phase contrast computed tomography.

FIG. 1 shows schematically and exemplarily an embodiment of an X-ray apparatus 10 for grating based phase contrast computed tomography. The X-ray apparatus 10 comprises a source-detector arrangement 11 with an X-ray source 12 for emittance of an X-ray beam of coherent or quasi-coherent radiation in a line pattern and further adapted for rotational movement around a rotation axis relative to an object placed on a table 14. Further, an X-ray detection system 16 is located opposite the X-ray source 12, wherein during a radiation procedure an object arranged on the table 14 can be moved along direction z parallel to the rotation axis to locate the object in a space 17 between the X-ray source 12 and the X-ray detection system 16. In general, it is possible to use axial acquisition (without movement of the patient) as well as a helix-type acquisition, i.e. an acquisition in which the patient is moved along direction z while the source-detector arrangement 11 is rotated. The X-ray detection system 16 is adapted to send data to a data processing unit or computing system 18, which preferably is connected to both the X-ray detection system 16 and the X-ray source 12. The computing system 18 may be located in the vicinity of the X-ray apparatus 10. Of course, it could also be located at a different place, such as a different laboratory. The X-ray source 12 and the X-ray detection system 16 are arranged on a gantry 13. The gantry 13 is adapted for rotational movement about the rotation axis relative to an object placed in the space 17.

Furthermore, a display device or console 20 is arranged in the vicinity of a table 14 to display information to the person operating the X-ray apparatus 10. Preferably, the display device 20 is movably mounted to allow for an individual adjustment depending on the examination situation. The display device 20 may also comprise an interface unit to input information by the user. The display device 20 is coupled to the computing system 18, which comprises a reconstruction processor 18a. The computing system 18 is coupled to a data repository 19, and both the computing system 18 and the data repository 19 are coupled to the X-ray apparatus 10.

Basically, the X-ray detection system 16 generates image data by exposing an object placed on the table 14 to an X-ray beam emitted by the X-ray source 12, wherein said image data is further processed in the X-ray apparatus 10 and the reconstruction processor 18a.

Figure 2:
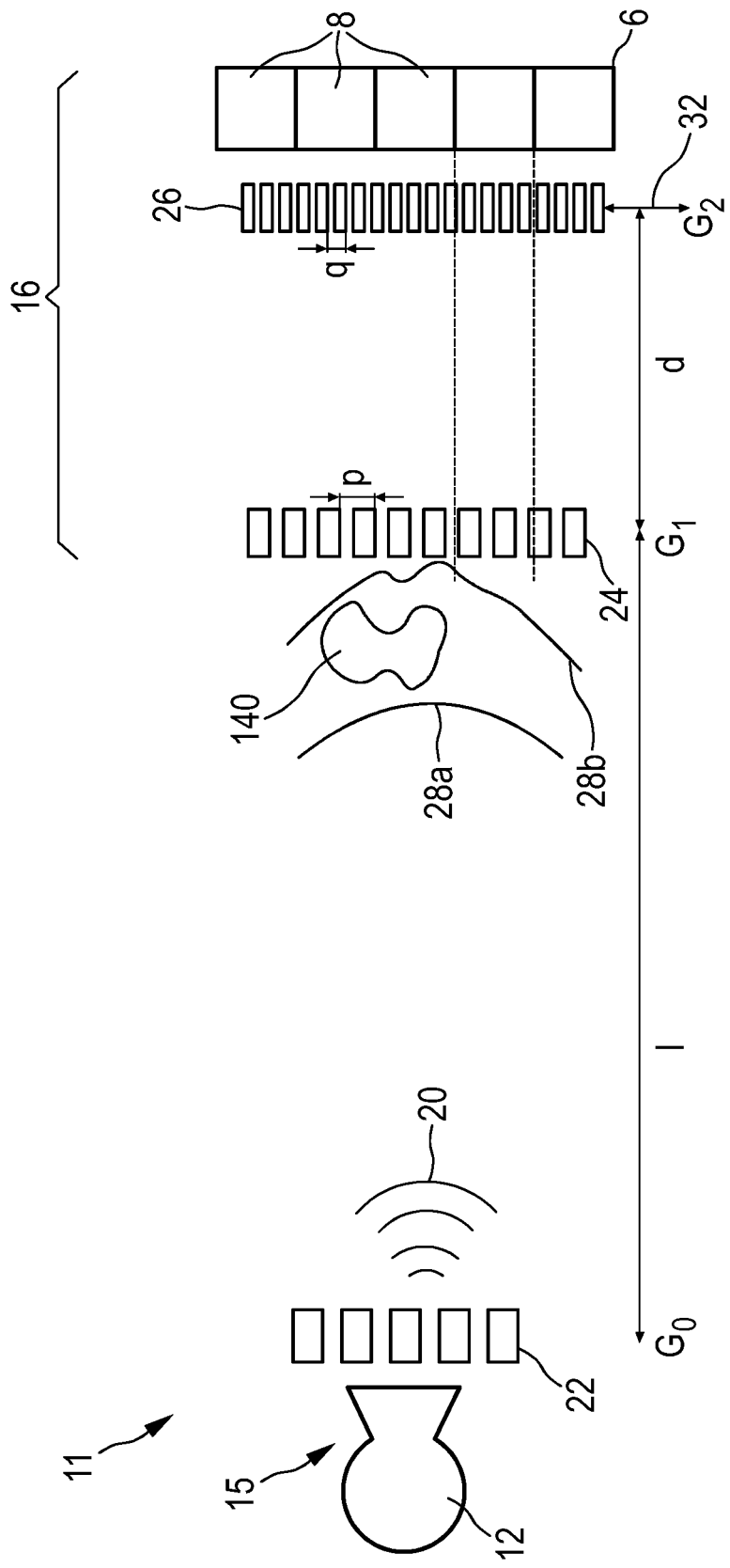
FIG. 2 shows schematically and exemplarily an embodiment of a source-detector arrangement for an X-ray apparatus for grating based phase contrast computed tomography.

FIG. 2 shows schematically and exemplarily an embodiment of an X-ray detection system 16 of a source-detector arrangement 11. In this arrangement, X-ray source 15 comprises an anode 12 and a source grating element 22 (also referred to as G0) to emit an X-ray beam 20 of coherent or quasi-coherent radiation. An object 140 is arranged in the path of the X-ray beam 20 between X-ray source 12 and X-ray detection system 16. X-ray detection system 16 comprises a first grating element or phase grating element 24 and a second grating element or analyzer grating element 26. First grating element 24 can also be referred to as G1 and second grating element 26 can also be referred to as G2. First grating element 24 is arranged in a distance 1 from X-ray source 12 with the source grating element 22 and the second grating element 26 is arranged at a distance d from the first grating element. Wave front 28a having a uniform phase is depicted as arriving at object 140 while a further phase front 28b having a change phase relationship within the wave front to a phase shift imposed on the wave front while penetrating the object 140 is depicted.

Subsequently, wave fronts arrive at the first grating element 24. The second grating element 26 is displaceable 32 relative to the first grating element 24 for acquisition of phase contrast images. However, it is also considerable to displace the first grating element 24 instead of analyzer grating element 26, or G0.

X-ray beam 20 passing through the first grating element 24, generating an interference pattern which is analyzed by the second grating element 26 in combination with the detector pixel elements 8.

For sake of clarity in FIG. 2, the first grating element 24 is depicted having a uniform pitch p and the second grating element 26 is depicted having a uniform pitch q. However, a detailed illustration regarding exemplary embodiments of the pitch arrangements of both the first and the second grating element may be taken from FIG. 12 or 13.

Figure 3:
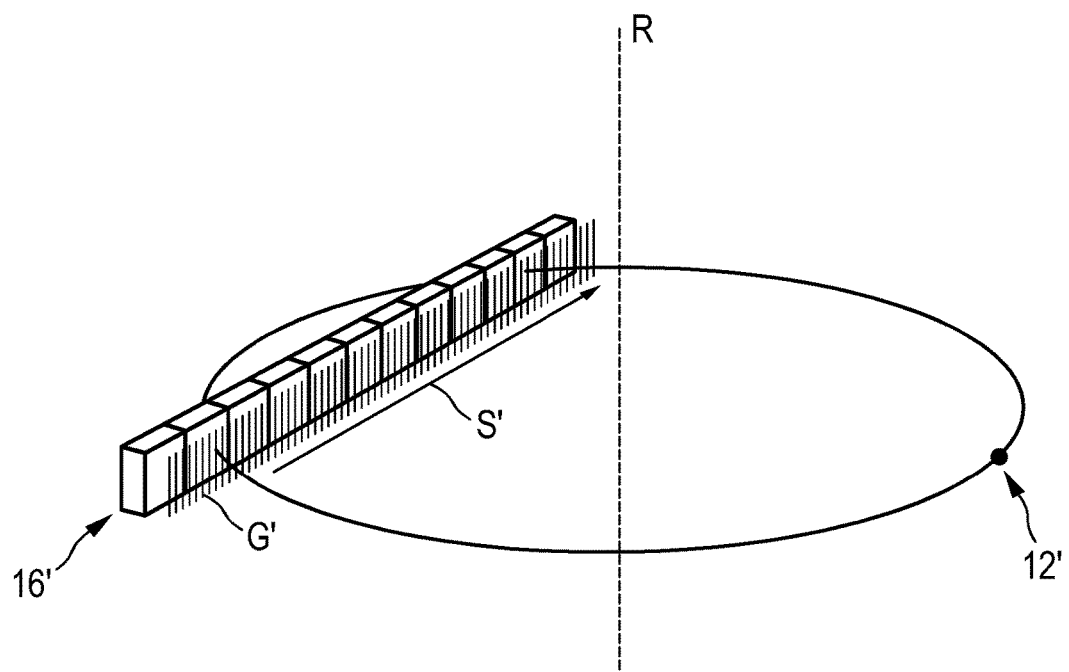
FIG. 3 shows schematically and exemplarily a conventional setup for a grating based differential phased contrast CT.

FIG. 3 shows schematically and exemplarily a conventional setup for grating based differential phase contrast CT with an X-ray source 12' and a detection system 16'. The first and second grating elements (for simplicity, FIG. 3 only shows one grating G') are aligned with the rotation axis R and the phase stepping direction S' lies within the plane of rotation.

Figure 4:
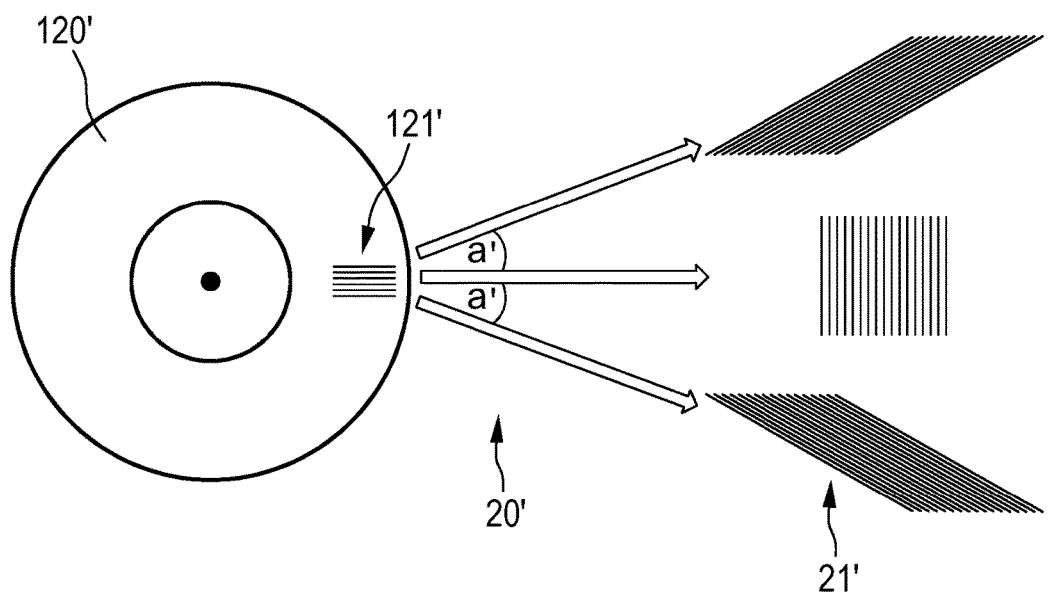
FIG. 4 shows schematically and exemplarily an anode of an X-ray source with a conventional X-ray line pattern.
Figure 5:
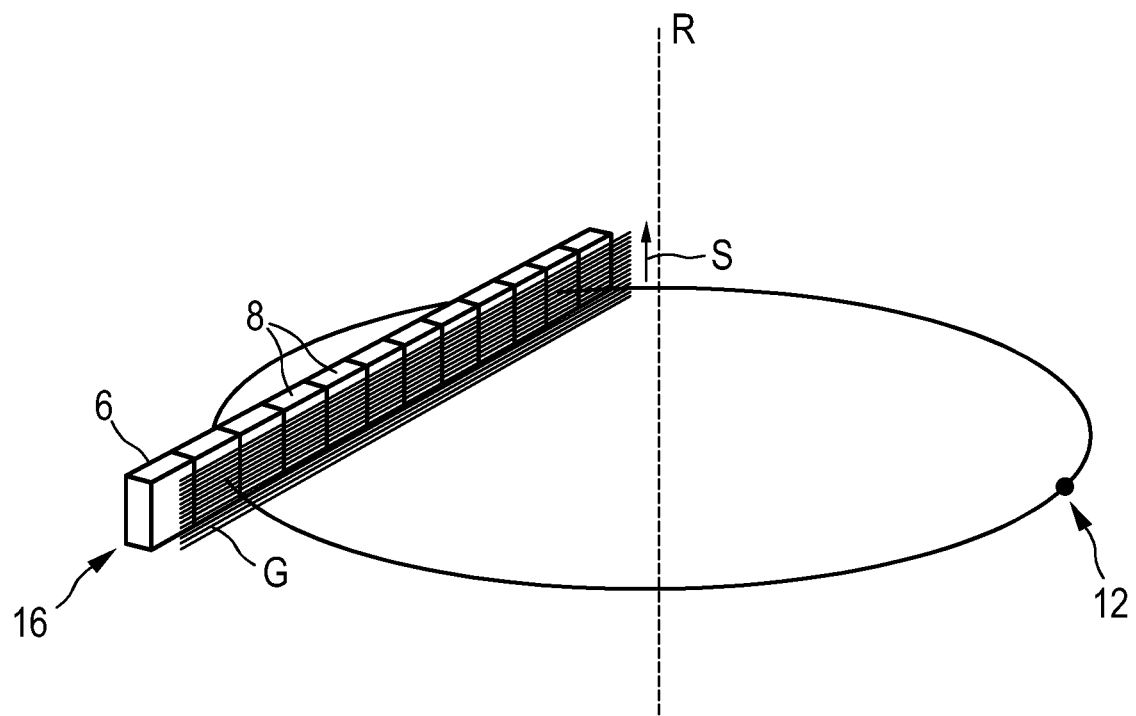
FIG. 5 shows schematically and exemplarily an embodiment of a phase contrast CT setup with a grating orientation according to the present invention.

Such a conventional setup shown in FIG. 3 may conventionally be used, as shown in FIG. 4, with an anode 120' of an X-ray source having a line pattern 121' for emitting radiation in a line pattern 21'. The line pattern 121' of the anode 120' looks like a vertical grating as seen along the optical axis of the arrangement (middle pattern on the right of FIG. 4). However, even for a rather small fan angle α' (15° in this illustration of FIG. 4) the projection of the line pattern 121' onto a detection system leads to a skewing of the pattern 21' which demands an according tilting of the first and second grating elements of the detection system. The anode 120' shown in FIG. 4 is assumed to have an anode angle of 8°. FIG. 5 shows schematically and exemplarily an embodiment of a setup for a grating based differential phase contrast CT with an X-ray source 12 and a detection system 16 with the first and second grating elements (for simplicity, in FIG. 5 only one grating G is shown) arranged in an orientation orthogonal to the rotation axis R. The phase stepping is performed in a phase stepping direction S parallel to the rotation axis R.

Existing filtered back-projection algorithms may be used to reconstruct the projection of the gradient of the object's real part of refractive index in direction of the rotation axis from the measurement of the gradient of the phase front in direction of the rotation axis by the detection system. The use of filtered back-projection algorithms is indicated in particular, when it is sufficient to reconstruct the first derivative of the electron density in the direction of the rotation axis. Alternatively or additionally, an iterative reconstruction algorithm may be used.

Figure 6:
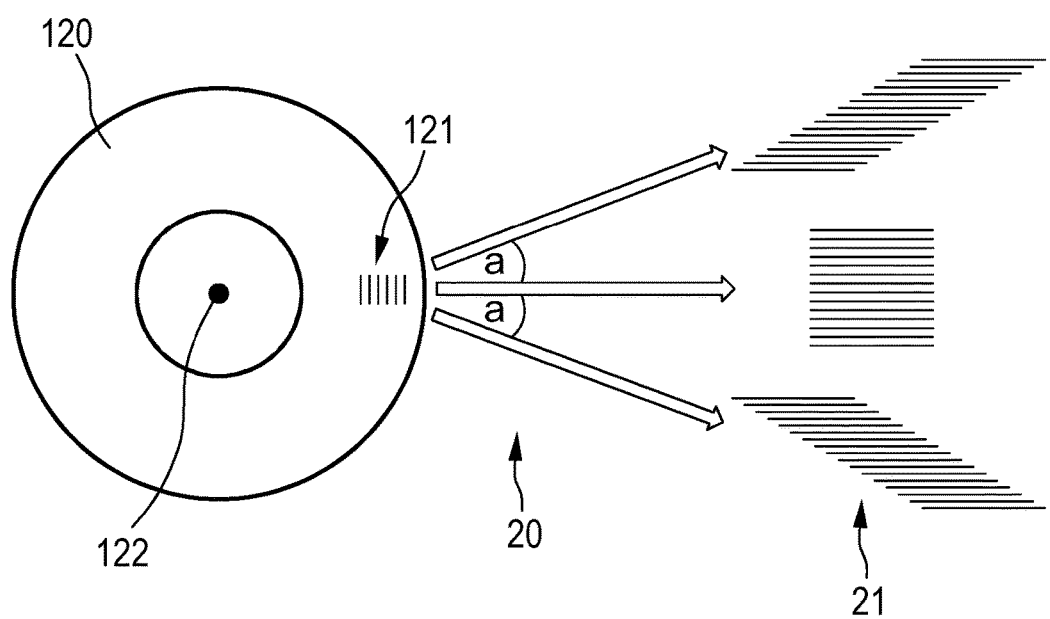
FIG. 6 shows schematically and exemplarily a top view of an embodiment of an anode of an X-ray source for emitting X-rays in a line pattern.
Figure 7:
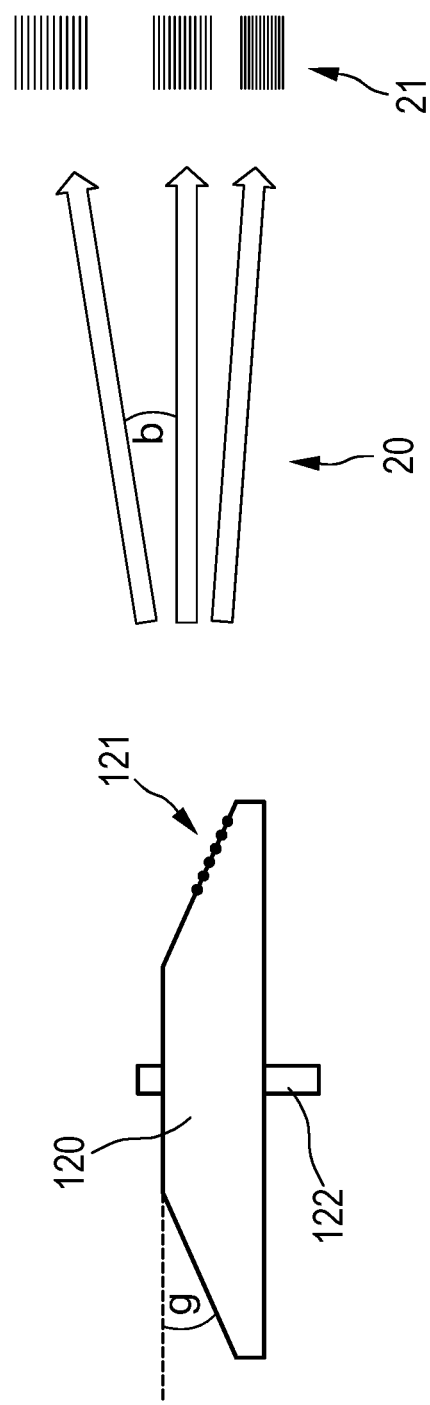
FIG. 7 shows a side view of the anode of FIG. 6.

FIGS. 6 and 7 show schematically and exemplarily an embodiment of an anode 120 in top view (FIG. 6) and side view (FIG. 7) for use in an X-ray source 12 according to FIG. 5. Anode 120 is of a rotary type and is arranged on a rotary shaft 122. The anode angle γ is again assumed to be 8°, which is however shown for clarity in FIG. 7 significantly enlarged. Rotary anode 120 is a structured anode which is adapted to emit an X-ray beam 20 of coherent or quasi-coherent radiation in a line pattern 21. Structured rotary anode 120 comprises strips 121 of different radiation emission, which are arranged parallel to the grating lines of the first and/or second gratings as indicated with G in FIG. 5. To compensate for mechanical tolerances and inaccuracies during the production process of mounting the anode on the anode shaft 122, the X-ray source 12 preferably is provided with a position sensor and a beam deflection unit with an integrated controller as further described with respect to FIG. 8 below.

The rotary anode 120 may also be unstructured and the line pattern is generated by forming electromagnetically directly the electron beam hitting the anode in a line pattern.

As can be seen from FIG. 6, by turning the line pattern 121 of the anode 120 by 90° compared to the conventional orientation shown in FIG. 4, the orientation of the projected line pattern 21 does not change anymore with the fan angle α. However, in such an arrangement, the effective pitch of the projected line pattern 21 varies with the cone angle θ as can be seen from FIG. 7. This is compensated in the detection system by a corresponding variation of the pitches of the first and second grating elements, as shown schematically and exemplarily in FIGS. 12 and 13.

Figure 8:
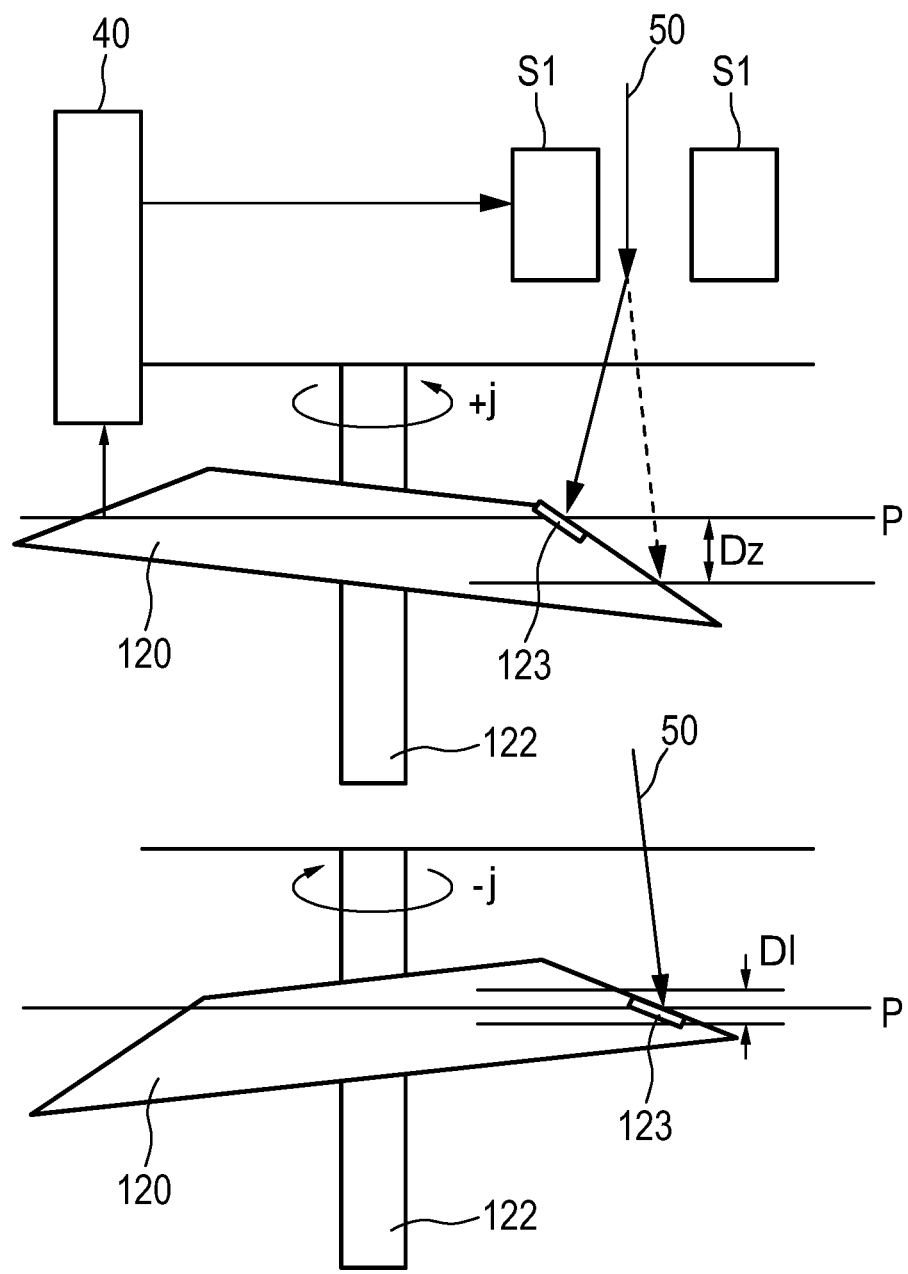
FIG. 8 shows schematically and exemplarily an embodiment of a rotating anode with compensation of the so-called wobble effect.

FIG. 8 shows schematically and exemplarily an embodiment of elements of an X-ray source including a system for measuring and compensating the periodical wobbling of the anode's inclination angle for use with the anode 120 of FIGS. 6 and 7, for example. In FIG. 8, a cross-sectional schematic view of an inclinedly mounted rotary anode 120 on a rotating anode shaft 122 is shown. This usually leads to a periodic position change of a focal spot 123 on the target surface of anode 120 such that the focal spot may be blurred. In FIG. 8, exemplarily two distinct phases of rotation of rotary anode 120 inclinedly mounted on its rotating anode shaft 122 in a cross-sectional schematic view are shown. These phases of rotation, which are shifted by a rotational angle of 180° against each other, show different inclination angles of the rotating anode 120 with respect to the rotational plane of the rotary anode. The rotational plane is oriented normal to the rotation axis of the rotating shaft 122. A position sensor 40 is provided to measure an anode phase resolved focal spot position for various conditions which may have an influence on the distorting wobble effect (e.g. through anode disk bending due to thermal conditions). Based upon this measurement, control data which are derived from the measurement results of the position sensor 40 are supplied to an integrated beam deflection unit 51 which is used to accordingly steer the electron beam 50 emitted by a cathode of the X-ray source. If the rotary anode 120 is rotated by 180° in +φ or −φ direction the position of the focal spot 123 is deviated by a deviation amplitude Δz in the direction of the anode shaft's rotational axis. Via the beam deflection unit 51, the electron beam 50 is steered such that the position of the focal spot 123 stays within the plane P of the center radiation fan beam. Without such a correction of the direction of electron beam 50, if Δz reaches a significant fraction of the projected focal spot diameter Δl, and if the X-ray pulse length is in the order of half the anode rotation period or longer, the X-ray image may be blurred.

Figure 9:
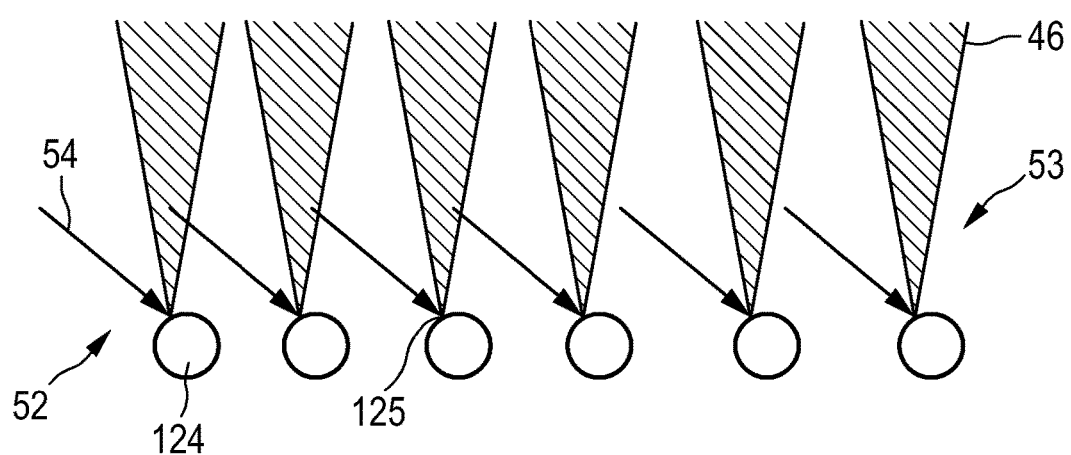
FIG. 9 shows schematically and exemplarily an embodiment of an X-ray source comprising a plurality of liquid metal jets.

FIG. 9 shows schematically and exemplarily an embodiment of the provision of liquid metal jets in an X-ray source for use in a setup of FIG. 5, for example. An electron beam structure 52 comprises a plurality 53 of individual electron beams 54 supplied as sub-electron beams. The pattern 46 indicates the generated radiation. The individual electron beams 54 are supplied to a plurality of liquid metal jets 124. These liquid metal jets 124 provide a plurality of focal lines 125 and form an anode structure resulting in a plurality of X-ray beams 46 to be used as an X-ray source.

Figure 10:
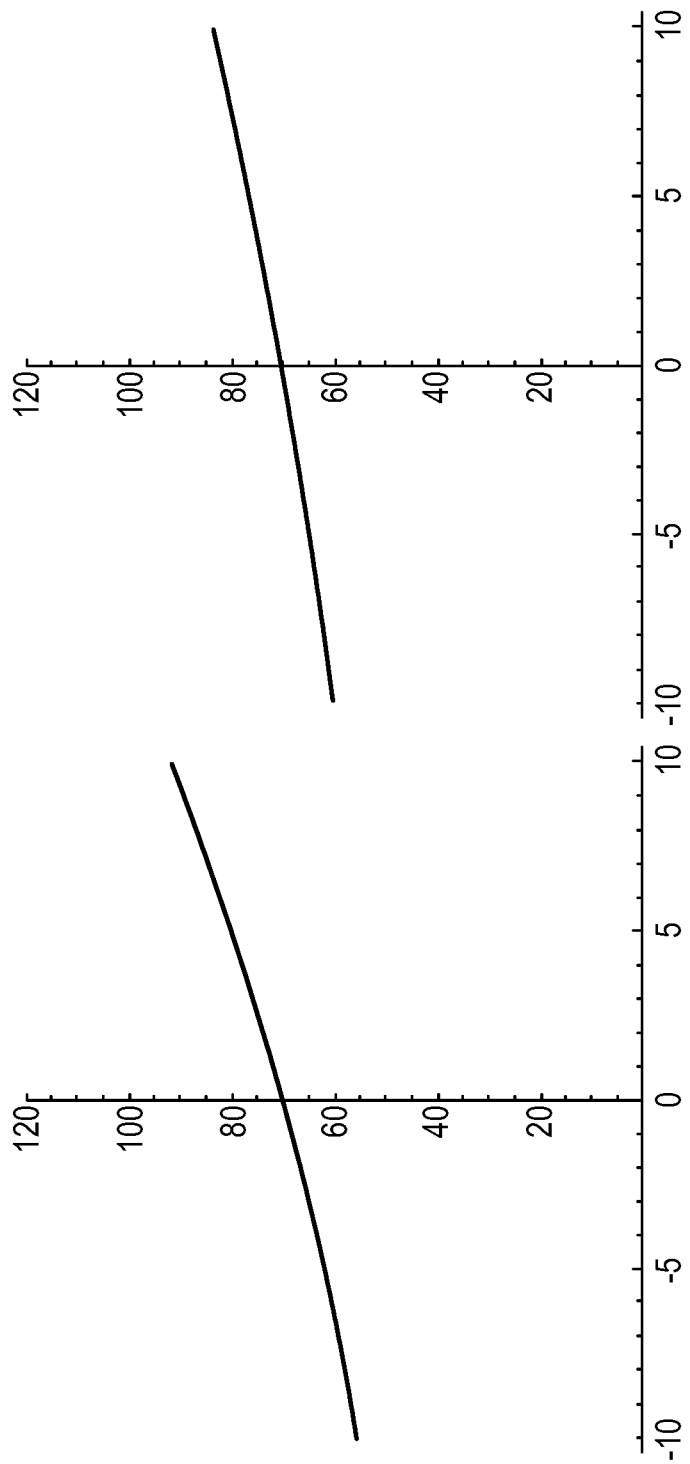
FIG. 10 shows schematically and exemplarily an energy dependence from the cone angle translated into a dependence on the systems coverage.

FIG. 10 shows schematically and exemplarily an energy dependence in keV on the vertical axis from the cone angle, which is translated into a dependence on the distance from the central plane, i.e., a dependence on the systems coverage, in mm on the horizontal axis. For the examples shown in FIG. 10, an example system geometry with an anode angle of 8° (left) or 12° (right), a distance between the X-ray source and the rotation axis of 570 mm and a design energy at 0° cone-angle of 70 keV has been assumed. As can be seen in FIG. 10, the variation of the grating pitch leads to a variation of the design energy from approximately 55 to 91 keV for a system with 20 mm coverage and an anode angle of 8°. Further, this variation depends strongly on the anode angle as can been seen from a comparison of the right and left part of FIG. 10, where the variation is reduced to a range of 60 to 83 keV by increasing the anode angle to 12°.

Figure 11:
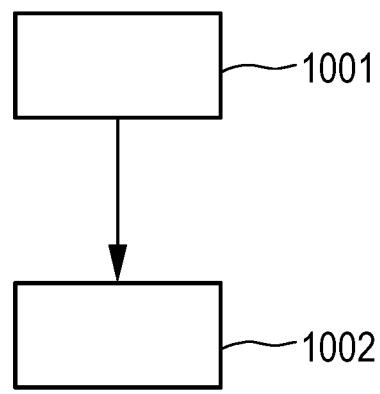
FIG. 11 shows a flowchart exemplarily illustrating an embodiment of a method for generating and detecting X-radiation.

FIG. 11 shows schematically and exemplarily an embodiment of method for generating and detecting an X-ray beam with a source-detector arrangement of an X-ray apparatus for grating based phase contrast computed tomography with the step 1001 of rotating an X-ray source emitting an X-ray beam of coherent or quasi-coherent radiation relative to an object around a rotation axis and the step 1002 of detecting the radiation by an X-ray detection system including a first grating element and a second grating element and a detector element, wherein the line pattern of the radiation and a grating direction of the grating elements are arranged orthogonal to the rotation axis; and wherein the first grating element has a first grating pitch varied dependent on a cone angle of the X-ray beam and the second grating element has a second grating pitch varied dependent on the cone angle of the X-ray beam.

Figure 12:
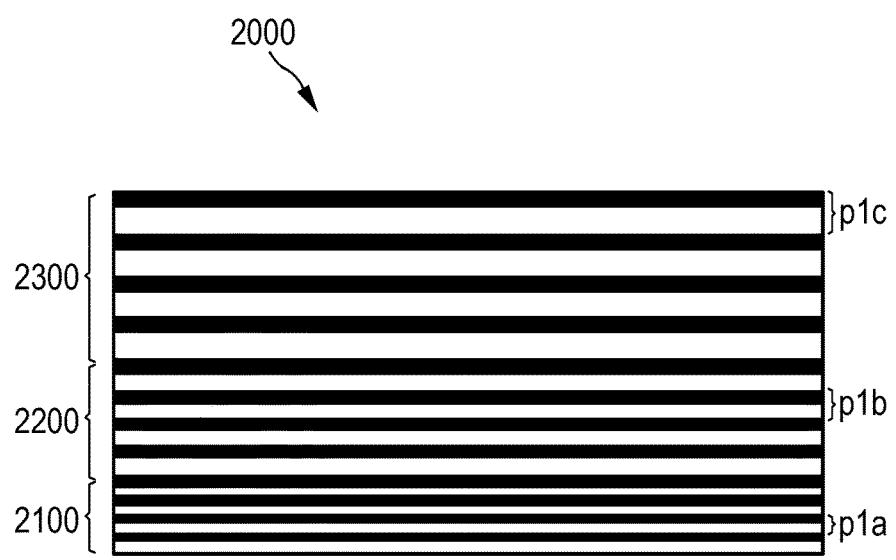
FIG. 12 shows schematically and exemplarily a first embodiment of a grating element of an X-ray detection system.

FIG. 12 shows schematically and exemplarily a first embodiment of a grating element 2000 of an X-ray detection system, which may be employed as a first and/or second grating element, with a grating pitch which is varied gradually or stepwise along the cone angle of the X-ray beam. The grating element 2000 shown in FIG. 12 has three different grating pitch sections 2100, 2200, 2300 with the same grating pitch within each one of the sections but with different grating pitches in different grating pitch sections. In other words, the grating pitch $p_{1a}$ of grating pitch section 2100 is the same within grating pitch section 2100, the grating pitch $p_{1b}$ of grating pitch section 2200 is the same within grating pitch section 2200, and the grating pitch $p_{1c}$ of grating pitch section 2300 is the same within grating pitch section 230. However, the gratings pitches $p_{1a}$, $p_{1b}$, $p_{1c}$ of the three grating pitch sections 2100, 2200, 2300 are different from one another, in particular, grating pitch $p_{1c}$ of grating pitch section 2300 is larger than grating pitch $p_{1b}$ of grating pitch section 2200, which again is larger than grating pitch $p_{1a}$ of grating pitch section 2100.

Figure 13:
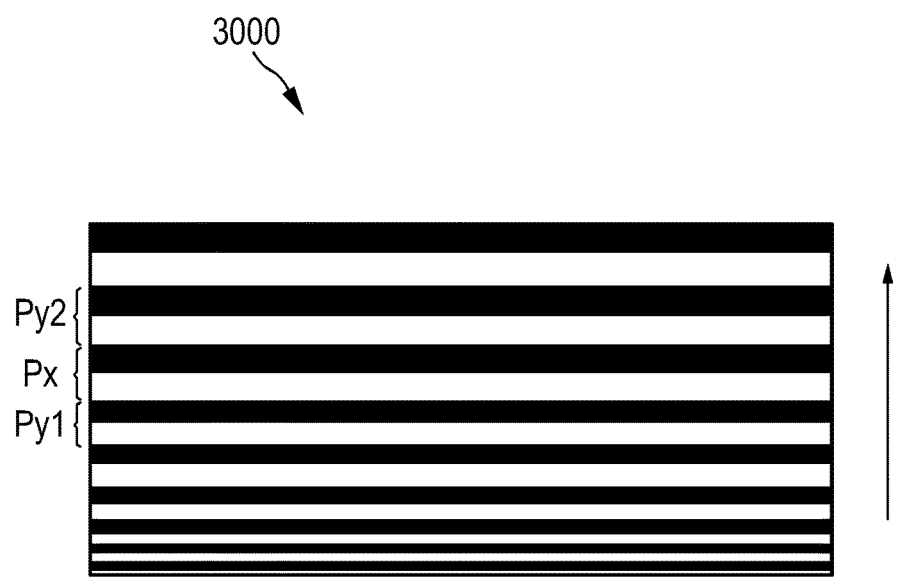
FIG. 13 shows schematically and exemplarily a second embodiment of a grating element of an X-ray detection system.

FIG. 13 shows schematically and exemplarily a second embodiment of a grating element 3000 of an X-ray detection system, which may be employed as a first and/or second grating element, with a grating pitch which is varied uniformly or monotonously along the cone angle of the X-ray beam. Each grating line of the grating element 3000 shown in FIG. 13 has a different grating pitch $p_x$ compared to adjacent grating lines $p_{y1}$, $p_{y2}$. In the embodiment shown in FIG. 13, the grating pitch $p_x$ increases with each grating line in a direction indicated with the arrow shown in FIG. 13.

It is furthermore to be pointed out that the medical computed tomography systems presented in this description are merely intended to be an example representation of an alternative application of the invention. At least one embodiment of the invention may likewise be used in conjunction with systems far examining biological or inorganic samples, without departing from the scope of this application. In particular, at least one embodiment of the invention may also be applicable to systems for material analysis.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like control of the source-detector arrangement or the X-ray apparatus in accordance with the method for generating and detecting an X-ray beam or for generating an image of an object, et cetera performed by one or several units or devices can be performed by any other number of units or devices. The control of the source-detector arrangement or the X-ray apparatus in accordance with the method for generating and detecting an X-ray beam or for generating an image of an object can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the internet or other wired or wireless telecommunication systems.

Any reference signs in the claims should not be construed as limiting the scope.

The invention relates to a source-detector arrangement of an X-ray apparatus for grating based phase contrast computed tomography. The source-detector arrangement comprises an X-ray source adapted for rotational movement around a rotation axis relative to an object and adapted for emittance of an X-ray beam of coherent or quasi-coherent radiation in a line pattern; and an X-ray detection system including a first grating element and a second grating element and a detector element; wherein the line pattern of the radiation and a grating direction of the grating elements are arranged orthogonal to the rotation axis; and wherein the first grating element has a first grating pitch varied dependent on a cone angle of the X-ray beam and/or the second grating element has a second grating pitch varied dependent on the cone angle of the X-ray beam.

The invention claimed is:

1. A source-detector arrangement of an X-ray apparatus for grating-based phase contrast computed tomography, comprising:
   an X-ray source configured to move around a rotation axis relative to an object and emit an X-ray beam of coherent or quasi-coherent radiation in a line pattern; and
   an X-ray detection system including a first grating element, a second grating element, and a detector element, wherein the line pattern of the radiation and a grating direction of the first and second grating elements are arranged orthogonally to the rotation axis, and wherein at least one of the first and second grating elements has a variable grating pitch varied dependent on a cone angle of the X-ray beam.

2. The source-detector arrangement according to claim 1, wherein the X-ray source comprises a source grating element with a grating direction arranged orthogonal to the rotation axis.

3. The source-detector arrangement according to claim 1, wherein the X-ray source includes an anode configured to emit the coherent or quasi-coherent radiation in the line pattern, the anode comprising a number of strips of different radiation emission; which are arranged parallel to the grating direction of the at least one of the first and second grating elements.

4. The source-detector arrangement according to claim 1, wherein the grating pitch is varied uniformly and/or gradually along the cone angle of the X-ray beam.

5. The source-detector arrangement according to claim 1, wherein the grating pitch is varied from a smaller grating pitch to a larger grating pitch along the cone angle of the X-ray beam.

6. The source-detector arrangement according to claim 1, wherein the grating element are arranged to be moveable relative to one another for providing phase stepping.

7. The source-detector arrangement according to claim 1, further comprising a rotary anode and a position sensor that is configured to measure a recurrent deviation of an actual position from a desired position of a focal spot of an electron beam on a target area of the rotary anode, and further comprising a beam deflection unit configured to deflect the electron beam based on the measured results provided by the position sensor.

8. The source-detector arrangement according to claim 1, further comprising a structured electron beam directed to an anode to emit the X-ray beam of the coherent or quasi-coherent radiation in the line pattern.

9. The source-detector arrangement according to claim 8, wherein the structured electron beam is adapted to be electromagnetically moveable for providing phase stepping.

10. The source-detector arrangement according to claim 1, further comprising a plurality of liquid metal jets providing a plurality of focal lines.

11. An X-ray apparatus for grating-based phase contrast computed tomography, comprising:
    a gantry; and
    a source-detector arrangement located on the gantry, comprising:
       an X-ray source configured to move around a rotation axis relative to an object and emit an X-ray beam of coherent or quasi-coherent radiation in a line pattern; and
       an X-ray detection system including a first grating element, a second grating element, and a detector element, wherein a line pattern of the radiation and a grating direction of the first and second grating elements are arranged orthogonally to the rotation axis, and wherein at least one of the first and second grating elements has a variable grating pitch dependent on a cone angle of the X-ray beam.

12. A method for generating and detecting an X-ray beam using a source-detector arrangement of an X-ray apparatus for grating-based phase contrast computed tomography, the method comprising:
    rotating an X-ray source emitting coherent or quasi-coherent radiation around a rotation axis relative to an object; and
    detecting the radiation by an X-ray detection system including a first grating element, a second grating element, and a detector element, wherein a line pattern of the radiation and a grating direction of the first and second grating elements are arranged orthogonally to the rotation axis, and wherein at least one of the first and second grating elements has a variable grating pitch dependent on a cone angle of the X-ray beam.

13. The method according to claim 12, further comprising phase stepping in a direction that is parallel to the rotation axis.

14. A non-transitory computer-readable medium having one or more executable instructions stored thereon, which, when executed by a processor, cause the processor to perform a method for generating and detecting an X-ray beam using a source-detector arrangement of an X-ray apparatus for grating-based phase contrast computed tomography, the method comprising:
    rotating an X-ray source emitting coherent or quasi-coherent radiation around a rotation axis relative to an object; and
    detecting the radiation by an X-ray detection system including a first grating element, a second grating element, and a detector element, wherein a line pattern of the radiation and a grating direction of the first and second grating elements are arranged orthogonally to the rotation axis, and wherein at least one of the first and second grating elements has a variable grating pitch dependent on a cone angle of the X-ray beam.

* * * * *